United States Patent
Krökel

(10) Patent No.: US 9,702,818 B2
(45) Date of Patent: Jul. 11, 2017

(54) DETECTION OF RAINDROPS ON A WINDOWPANE BY MEANS OF CAMERA AND LIGHT

(71) Applicant: Conti Temic Microelectronic GmbH, Nürnberg (DE)

(72) Inventor: Dieter Krökel, Eriskirch (DE)

(73) Assignee: Conti Temic microelectronic GmbH, Nürnberg (DE)

( * ) Notice: Subject to any disclaimer, the term of this patent is extended or adjusted under 35 U.S.C. 154(b) by 0 days.

(21) Appl. No.: 14/379,396

(22) PCT Filed: Apr. 26, 2013

(86) PCT No.: PCT/DE2013/100155
§ 371 (c)(1),
(2) Date: Aug. 18, 2014

(87) PCT Pub. No.: WO2013/163991
PCT Pub. Date: Nov. 7, 2013

(65) Prior Publication Data
US 2015/0034827 A1   Feb. 5, 2015

(30) Foreign Application Priority Data
May 3, 2012   (DE) .................. 10 2012 103 873

(51) Int. Cl.
*G01N 21/55* (2014.01)
*B60S 1/08* (2006.01)
(Continued)

(52) U.S. Cl.
CPC ............ *G01N 21/55* (2013.01); *B60S 1/0844* (2013.01); *G01N 21/94* (2013.01);
(Continued)

(58) Field of Classification Search
CPC   B60S 1/0844; G06K 9/00791; G01N 21/552; G01N 21/55; G01N 21/94; G01N 2021/945; G01N 2201/062
(Continued)

(56) References Cited

U.S. PATENT DOCUMENTS

| | | |
|---|---|---|
| 4,515,443 A | 5/1985 | Bly |
| 4,741,605 A | 5/1988 | Alfredsson |

(Continued)

FOREIGN PATENT DOCUMENTS

| | | |
|---|---|---|
| DE | 4417385 | 11/1995 |
| DE | 19504606 | 8/1996 |

(Continued)

OTHER PUBLICATIONS

International Search Report for PCT/DE2013/100155 mailed Jul. 24, 2013.
(Continued)

*Primary Examiner* — David Porta
*Assistant Examiner* — Blake Riddick
(74) *Attorney, Agent, or Firm* — RatnerPrestia

(57) ABSTRACT

A device and to a method for detecting rain, which includes a camera and a light source. The camera is arranged behind a windowpane, in particular inside a vehicle, behind a windscreen, and focused on a far range located in front of the windowpane. The light source for producing at least one light beam which is directed to the windowpane directs the at least one light beam to the windowpane in such a manner that at least one beam which is reflected by the outer side of the windowpane is incident on the camera. The structure of the image of the at least one beam reflected by the outer side of the windowpane is analyzed, in particular as part of an image processing step. The type of rain or precipitation on
(Continued)

the outer side of the windowpane is classified based on the analysis of the structure of this image.

13 Claims, 5 Drawing Sheets

(51) Int. Cl.
    *G01N 21/94*     (2006.01)
    *G06K 9/00*     (2006.01)
    *G01N 21/552*     (2014.01)

(52) U.S. Cl.
    CPC ....... *G06K 9/00791* (2013.01); *G01N 21/552* (2013.01); *G01N 2021/945* (2013.01); *G01N 2201/062* (2013.01)

(58) Field of Classification Search
    USPC .............................................. 250/341.8, 574
    See application file for complete search history.

(56) References Cited

U.S. PATENT DOCUMENTS

| | | | |
|---|---|---|---|
| 5,498,866 A * | 3/1996 | Bendicks | B60S 1/0822 250/227.25 |
| 5,923,027 A | 7/1999 | Stam | |
| 5,987,152 A | 11/1999 | Weisser | |
| 6,137,529 A | 10/2000 | Kunimitsu | |
| 6,331,819 B1 | 12/2001 | Hog | |
| 6,376,824 B1 | 4/2002 | Michenfelder | |
| 6,392,218 B1 | 5/2002 | Kuehnle | |
| 6,452,148 B1 | 9/2002 | Bendicks | |
| 6,555,804 B1 | 4/2003 | Blasing | |
| 6,614,015 B1 | 9/2003 | Ba | |
| 6,617,564 B2 | 9/2003 | Ockerse | |
| 6,727,342 B1 * | 4/2004 | Bastioli | C08L 67/02 428/35.1 |
| 6,841,767 B2 | 1/2005 | Mindl | |
| 6,968,073 B1 | 11/2005 | O'Boyle | |
| 7,208,962 B2 | 4/2007 | Sun | |
| 7,253,898 B2 | 8/2007 | Saikalis | |
| 7,259,367 B2 | 8/2007 | Reime | |
| 7,609,857 B2 | 10/2009 | Franz | |
| 7,612,356 B2 | 11/2009 | Utida | |
| 7,646,889 B2 | 1/2010 | Tsukamoto | |
| 7,855,353 B2 | 12/2010 | Blaesing | |
| 7,863,568 B2 | 1/2011 | Fleury | |
| 8,274,562 B2 | 9/2012 | Walter | |
| 8,541,732 B2 | 9/2013 | Rothenhaeusler | |
| 8,913,132 B2 | 12/2014 | Seger | |
| 8,913,133 B2 | 12/2014 | Huelsen | |
| 2002/0003571 A1 | 1/2002 | Schofield | |
| 2002/0020804 A1 * | 2/2002 | Bauer | B60R 1/088 250/214 C |
| 2002/0081029 A1 | 6/2002 | Marugame | |
| 2002/0121972 A1 * | 9/2002 | Schofield | B60H 1/00785 340/438 |
| 2002/0148987 A1 * | 10/2002 | Hochstein | 250/573 |
| 2003/0066955 A1 | 4/2003 | Schaub | |
| 2003/0201380 A1 | 10/2003 | Ockerse | |
| 2004/0004456 A1 | 1/2004 | LeBa | |
| 2004/0164981 A1 | 8/2004 | Fujita | |
| 2004/0165749 A1 * | 8/2004 | Holz et al. | 382/104 |
| 2005/0035926 A1 * | 2/2005 | Takenaga et al. | 345/8 |
| 2005/0063071 A1 | 3/2005 | Wang | |
| 2005/0206511 A1 * | 9/2005 | Heenan et al. | 340/438 |
| 2005/0231725 A1 | 10/2005 | Franz | |
| 2005/0254688 A1 * | 11/2005 | Franz | 382/104 |
| 2006/0076477 A1 * | 4/2006 | Ishikawa | 250/227.25 |
| 2006/0163458 A1 * | 7/2006 | Reime | B60S 1/0822 250/227.25 |
| 2006/0191215 A1 | 8/2006 | Stark | |
| 2007/0075220 A1 | 4/2007 | Kotani | |
| 2007/0216768 A1 | 9/2007 | Smith | |
| 2007/0267993 A1 * | 11/2007 | Leleve et al. | 318/483 |
| 2007/0268470 A1 | 11/2007 | Shibazaki | |
| 2008/0027607 A1 | 1/2008 | Ertl | |
| 2008/0049344 A1 | 2/2008 | DeWard | |
| 2008/0085755 A1 | 4/2008 | Okada | |
| 2008/0185603 A1 | 8/2008 | Itoi | |
| 2008/0265134 A1 | 10/2008 | Kinoshita | |
| 2008/0283782 A1 * | 11/2008 | Blaesing | B60R 11/04 250/573 |
| 2008/0296577 A1 | 12/2008 | Yuan | |
| 2009/0085755 A1 | 4/2009 | Schafer | |
| 2009/0128629 A1 | 5/2009 | Egbert | |
| 2009/0201366 A1 | 8/2009 | Sase | |
| 2010/0208060 A1 | 8/2010 | Kobayashi | |
| 2011/0031921 A1 * | 2/2011 | Han | 318/483 |
| 2011/0043624 A1 | 2/2011 | Haug | |
| 2011/0128543 A1 * | 6/2011 | Choi | 356/342 |
| 2011/0204206 A1 * | 8/2011 | Taoka | 250/208.1 |
| 2011/0253917 A1 | 10/2011 | Rothenhaeusler | |
| 2011/0273564 A1 | 11/2011 | Seger | |
| 2011/0280026 A1 * | 11/2011 | Higgins-Luthman | B60Q 1/143 362/466 |
| 2012/0026318 A1 * | 2/2012 | Huelsen | B60S 1/0844 348/135 |
| 2012/0026330 A1 | 2/2012 | Huelsen | |
| 2012/0153154 A1 | 6/2012 | Rothenhaeusler | |
| 2013/0235381 A1 * | 9/2013 | Kroekel et al. | 356/445 |
| 2014/0300738 A1 | 10/2014 | Mueller | |
| 2014/0321709 A1 * | 10/2014 | Kasahara et al. | 382/103 |
| 2015/0034827 A1 | 2/2015 | Krokel | |

FOREIGN PATENT DOCUMENTS

| | | |
|---|---|---|
| DE | 19704818 | 8/1997 |
| DE | 20207170 | 8/2002 |
| DE | 10230200 | 1/2004 |
| DE | 19700665 | 7/2004 |
| DE | 10303046 | 10/2004 |
| DE | 10316794 | 11/2004 |
| DE | 10322010 | 12/2004 |
| DE | 10355205 | 7/2005 |
| DE | 102004015040 | 10/2005 |
| DE | 102004037871 | 3/2006 |
| DE | 102005004513 | 3/2006 |
| DE | 102006016774 | 10/2006 |
| DE | 102006008274 | 8/2007 |
| DE | 102006010671 | 9/2007 |
| DE | 102006022404 | 11/2007 |
| DE | 102007061725 | 6/2009 |
| DE | 102008043737 | 5/2010 |
| DE | 102009000003 | 7/2010 |
| DE | 102009000004 | 7/2010 |
| DE | 102009000005 | 7/2010 |
| EP | 0832798 | 4/1998 |
| EP | 1440856 | 7/2004 |
| EP | 1507138 | 2/2005 |
| EP | 1580092 | 9/2005 |
| EP | 1707946 | 10/2006 |
| EP | 1764835 | 3/2007 |
| EP | 1923695 | 5/2008 |
| JP | 574133 | 1/1982 |
| JP | 0461379 | 2/1992 |
| JP | 11234474 | 8/1999 |
| JP | 2003315256 | 11/2003 |
| JP | 2005292544 | 10/2005 |
| JP | 2006184844 | 7/2006 |
| JP | 2007309655 | 11/2007 |
| JP | 2009092453 | 4/2009 |
| JP | 2009098477 | 5/2009 |
| JP | 2010096604 | 4/2010 |
| WO | 03029757 | 4/2003 |
| WO | 03060826 | 7/2003 |
| WO | 2003097420 | 11/2003 |
| WO | 2005075248 | 8/2005 |
| WO | 2006015905 | 2/2006 |
| WO | 2006024247 | 3/2006 |
| WO | 2006121954 | 11/2006 |
| WO | 2009020918 | 2/2009 |
| WO | 2010072198 | 7/2010 |

(56) References Cited

FOREIGN PATENT DOCUMENTS

| | | |
|---|---|---|
| WO | 2010076064 | 7/2010 |
| WO | 2010076066 | 7/2010 |
| WO | 2012163341 | 12/2012 |

OTHER PUBLICATIONS

International Preliminary Report on Patentability and English translation of the Written Opinion of the International Searching Authority for International Application No. PCT/DE2011/001749 mailed Jun. 4, 2013.

International Search Report for International Application No. PCT/DE2011/001749 mailed Mar. 29, 2012.

* cited by examiner under one piece of prior art but not under another.

DETECTION OF RAINDROPS ON A WINDOWPANE BY MEANS OF CAMERA AND LIGHT

CROSS REFERENCE TO RELATED APPLICATIONS

This application is the U.S. National Phase Application of PCT International Application No. PCT/DE2013/100155, filed Apr. 26, 2013, which claims priority to German Patent Application No. 10 2012 103 873.2, filed May 3, 2012, the contents of such applications being incorporated by reference herein.

FIELD OF THE INVENTION

The invention relates to a method for detecting raindrops on a windowpane by means of a light source and a camera.

BACKGROUND OF THE INVENTION

WO2010/072198 A1, which is incorporated by reference, describes a method for detecting rain with the aid of a camera, which is used for automotive driver assistance functions. To detect rain, a bifocal optical system is used which produces a sharp image of a partial area of the windscreen on a partial area of the imager or image sensor of the camera. In order to be able to detect raindrops even at night, it is further proposed to couple light into the windscreen using a coupling-in element and to transfer this light within the screen by means of total internal reflection. The light which has been entirely reflected is then coupled out towards the camera by a coupling-out element. When there are drops of water on the windscreen, part of the light is coupled out rather than reflected to the coupling-out element.

U.S. Pat. No. 7,259,367 B2, which is incorporated by reference, also proposes a method for sensing rain by means of a camera, wherein a large area of the window of view, which is defined by the camera's angular aperture and the windowpane, is illuminated. The camera is almost set to infinity focus and can thus be used for driver assistance applications at the same time. As an image of the far range is produced, raindrops can only be noticed as faults in the image, which are detected by complex difference measurements of the images recorded using light that is pulsed or modulated in synchronization with the pixel frequency.

SUMMARY OF THE INVENTION

An aspect of the present invention provides more reliable and precise information relating to rain or moisture on the windowpane, compared to methods known from the state of the art.

This is achieved by means of a method for detecting rain on the outer side of a windowpane. By means of a camera which is arranged behind the windowpane and focused on a far range in front of the windowpane, and a light source for producing at least one light beam which is directed on the windowpane. The light source directs the at least one light beam to the windowpane in such a manner that at least one beam which is reflected by the outer side of the windowpane is incident on the camera. The camera records an image of the at least one beam reflected by the outer side of the windowpane. The structure of the image of the at least one beam reflected by the outer side of the windowpane is analyzed, in particular as part of an image processing step, in order to classify the type of rain or precipitation on the outer side of the windowpane.

An aspect of the invention has the advantage that the type of rain or precipitation can be determined with a vehicle camera, in particular a driver assistance camera, while hardly affecting the main function of the camera.

According to a preferred method, the analysis of the structure of the image of the at least one beam reflected by the outer side of the windowpane comprises the detection of a pattern or texture. The detection of a texture and/or pattern may, in particular, be a classification using trained textures and/or patterns, e.g. by means of a neural network.

In a preferred embodiment, the analysis of the structure of the image of the at least one beam reflected by the outer side of the windowpane comprises a comparison of present with stored and/or learned structural characteristics.

According to an advantageous embodiment, the presence of an individual raindrop on the outer side of the windowpane is deduced from a continuous partial area with low intensity in the image of the at least one beam reflected by the outer side of the windowpane.

Preferably, the presence of drizzle or light rain falling in very fine drops on the outer side of the windowpane is deduced from streaks in the image of the at least one beam reflected by the outer side of the windowpane.

In an advantageous embodiment variant, the light source directs the at least one light beam to the windowpane in such a manner that beams which are reflected by the inner side and outer side of the windowpane are incident on the camera as at least two spatially separated beams. As a result, the camera records an image of the at least one beam reflected by the outer side of the windowpane and an image of the at least one beam reflected by the inner side of the windowpane. The latter may be analyzed as a reference image.

In this variant, an analysis of the image of the at least one beam reflected by the inner side of the windowpane preferably enables condensation or another circumstance affecting optical characteristics to be detected on the inner side of the windowpane.

To this end, the structure or the amount of light of the image of the at least one beam reflected by the inner side of the windowpane may advantageously be analyzed.

According to a preferred configuration of the method, the camera initially records a first image while the light source is switched off. Then a second image is recorded while the light source is switched on. The difference image of the first and the second image is produced. In the difference image, the structure of the image of the at least one beam reflected on the outer side of the windowpane is analyzed in order to identify the type of precipitation or rain on the outer side of the windowpane.

If, advantageously, the light used is visible light, it must be ensured that the light does not confuse other road users.

To this end, it is proposed to use a short visible light pulse whose intensity is adapted to external brightness. This would require only a short exposure time and image recording time for the rain sensor image, so that the driver assistance function is hardly affected. In daylight, such a light pulse would only be noted by a person looking directly at the light. At night, only little light is needed to detect rain. This means, the intensity can be reduced to an appropriate level, so that the light is not annoying.

A preferred adaptation of the light intensity—regardless of the wavelength range used—has another advantage. By day the light reflections intended for the rain sensor are well visible, and at night the images are prevented from becoming saturated, which would make it impossible to analyze the structure of the image(s).

Advantageously, it may be detected how the structures of the beam reflected on the outer side of the windowpane, which are recorded by the image sensor of the camera, change over time. To this end, the camera may record a sequence of images.

Preferably, the camera is used for one or more other driver assistance functions which are based on an analysis of the focused image of the far range.

An aspect of the invention further relates to a device for detecting rain or precipitation, which comprises a camera and a light source. The camera is arranged behind a windowpane, in particular inside a vehicle, e.g. behind a windscreen, and focused on a far range located in front of the windowpane. The camera preferably comprises an objective used for focusing, and an image sensor, e.g. a CCD sensor or CMOS sensor. The light source for producing at least one light beam directed to the windowpane directs the at least one light beam to the windowpane in such a manner that at least one beam (or partial beam of the light beam directed to the windowpane) which is reflected by the outer side of the windowpane is incident on the camera. The light source may be designed as one or more light-emitting diodes (LEDs) or as a strip light. Image processing means are provided to analyze the structure of the image of the at least one beam reflected by the outer side of the windowpane. Means for classifying the type of rain or precipitation on the outer side of the windowpane are provided, whose classification is based on the analysis of the structure of this image.

In a preferred embodiment, the light source directs the at least one light beam to the windowpane in such a manner that the beams which are reflected by the inner and the outer side of the windowpane are incident on the camera as at least two spatially separated beams. As a result, the at least two beams which are incident on the camera can produce two spatially separated images. The structure of the separate light reflections can be analyzed. The beam which is reflected (directly) on the inner side of the windowpane and is incident on the camera may preferably be used as a reference image since the structure of the image of this beam will not change, regardless of whether there are raindrops on the outer side of the windowpane or not. Changes in the structure of the image of this beam suggest condensation or the like on the inner side of the windowpane.

The light may advantageously be provided by individual light-emitting diodes, which are e.g. arranged in series. As an alternative, a strip light could be used. Preferably, a sufficiently directed radiation pattern, e.g. of less than ±20°, is ensured.

According to a preferred configuration of the invention, the light source is structurally integrated in the camera or the camera housing. In this case, the light source may preferably be arranged within the camera housing, below a diaphragm or a funnel defining the camera's view.

Advantageously, the light source produces light in the infrared wavelength range, and the diaphragm allows light in the infrared wavelength range to pass through, at least in a partial area thereof which is located above the light source or in the direction of irradiation of the light source.

The light source may, in particular, be arranged on a circuit carrier or circuit board of the camera.

Preferably, the light source only produces light whose wavelength is in a particular wavelength range, e.g. in the (near) infrared wavelength range. In the beam path of the camera, a first spectral filter is arranged in the area where the at least two spatially separated beams are reflected. The first spectral filter generally allows light with a wavelength in this particular wavelength range to pass through (e.g. transmits infrared light).

Advantageously, a second spectral filter is arranged in the area of the beam path where the at least two spatially separated beams are not reflected, and the second spectral filter blocks light whose wavelength is in the particular wavelength range (e.g. infrared-blocking filter)

The first or both spectral filter(s) may preferably be provided directly on pixels of the image sensor of the camera.

In an advantageous embodiment, the light source produces a focused light beam.

Preferably, the light beam produced by the light source may be directed to the windowpane by means of an optical waveguide, such as a glass fibre.

BRIEF DESCRIPTION OF THE DRAWINGS

The invention will now be explained in more detail with reference to figures and exemplary embodiments.

In the figures.

DETAILED DESCRIPTION OF THE PREFERRED EMBODIMENTS

Figure 1:
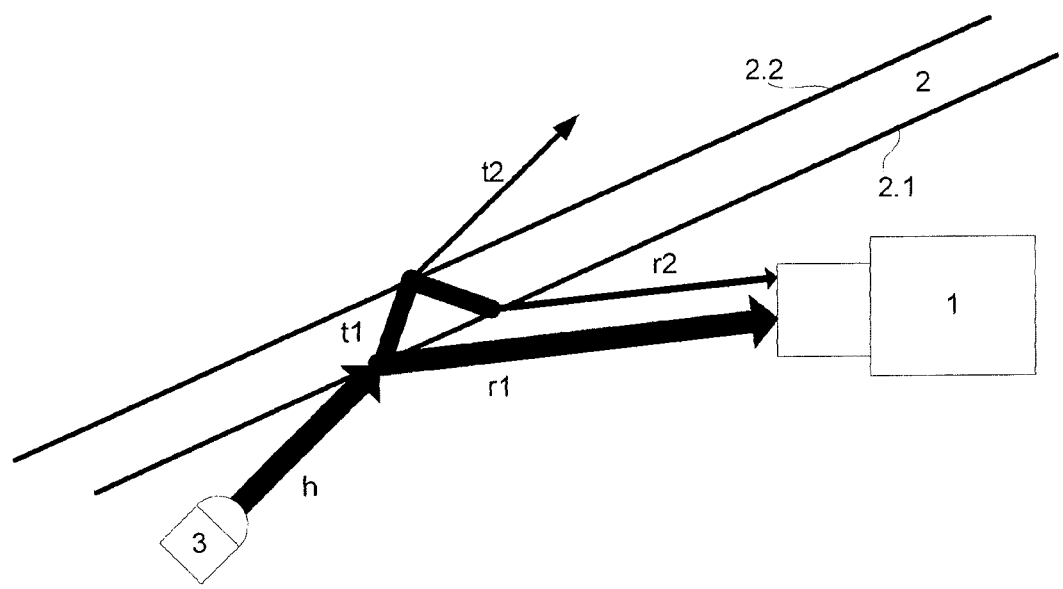
FIG. 1 schematically shows the basic principle of a potential arrangement of the light source and the camera, indicating the beam paths in case of a dry windowpane.

FIG. 1 illustrates the functional principle of an embodiment of the invention. The method for detecting rain shown here is based on a camera (1) which is focused on the far range, and a light (3). A light beam (h) produced by a light source (3) is directed to the windowpane (2) in such a manner that the beams reflected by the inner side (2.1) and outer side (2.2) of the windowpane are incident on the objective or the camera (1) as two spatially separated beams (r1, r2). As the camera is focused on the far range, the periphery of the focused beams is shown blurred on the imager. However, both beams (r1, r2) are sufficiently separate, and their images (8, 9) (hereinafter also called light reflections) are recorded by the image sensor.

The light emitted by the light source may be focused. The portion (r1) of the main beam which is reflected on the air-windowpane interface (or inner side (2.1) of the windowpane) serves as a reference beam. The portion which is transmitted (t1) into the windowpane comprises a portion which is reflected on the windowpane-air interface (or outer side (2.2) of the windowpane) and is incident on the camera (1); this portion serves as the measuring beam (r2). The figure does not show the portion of the beam which is reflected several times within the windowpane (2) (on the inner side (2.1), windowpane-air, after it has been reflected on the outer side (2.2), windowpane-air).

Figure 2:
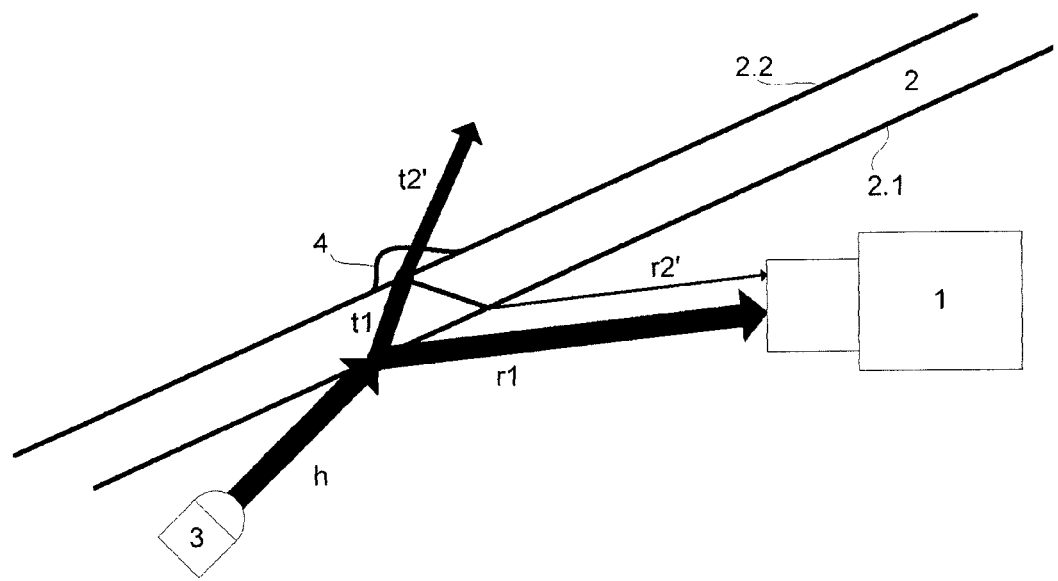
FIG. 2 schematically shows the beam paths which have changed due to rain on the windowpane.

The changes produced in the image of the measuring beam in case of rain (4) on the outer side (2.2) of the windowpane will be explained with reference to FIG. 2. When there is rain (4) on the outer side (2.2) of the windscreen (2), the major part of the light (t1) is coupled out, so that the reflected portion (r2') is reduced accordingly (see FIG. 2). The beam (r1) which is reflected by the inner side (2.1) is not affected by this circumstance.

Based on a comparison of the images of the measuring beam (r2 or r2') with and without precipitation (4) on the outer side (2.2) of the windowpane and an analysis of the structure of the image of the measuring beam, the type of precipitation (4) can be identified, and a windscreen wiper can be activated accordingly.

To prevent the light (3) from confusing the driver and other road users, near-infrared light may, in particular, be used, to which the CCD imagers or CMOS imagers normally used are highly sensitive.

To ensure non-sensitivity to adverse factors, such as noise, daylight and sunlight as well as other artificial sources of light, a partial or complete temporal modulation of the light source (3), preferably in synchronization with the image readout frequency, is proposed, so that any interference can be subtracted using simple difference methods. This is one approach to improving the signal-to-noise ratio. Another option is suitable spectral filtering: the part of the imager on which the beam pairs (r1, r2/r2') are incident may be provided with a spectral band-pass with high transmittance for the wavelength of the light (3).

Figure 3:
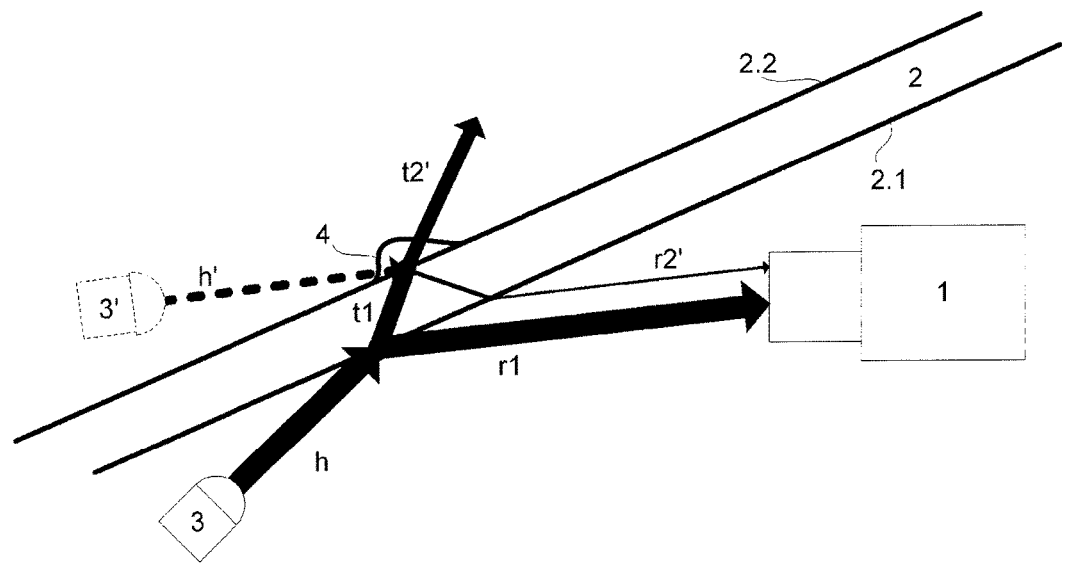
FIG. 3 shows the changed beam paths and a mirror image of the light source.

FIG. 3 serves to illustrate the fact that the light reflection (9) of the measuring beam (r2 or r2') appears as a blurry image of the light source (3), which is mirrored on the outer side of the windowpane. The mirror images of the light source (3') and of the light beam (h') are shown schematically by dashed lines.

Figure 4A:
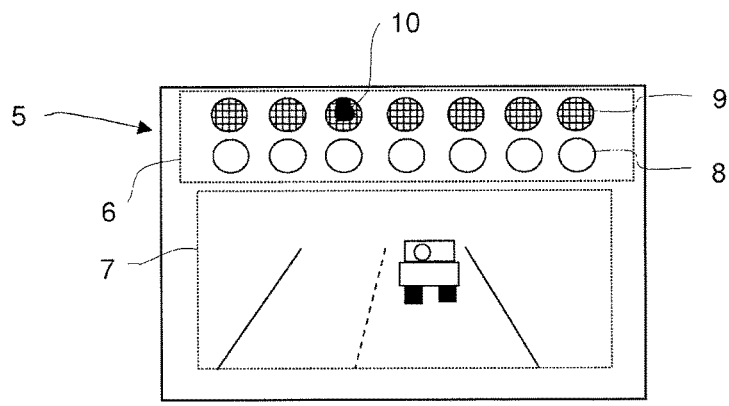
FIGS. 4a and 4b show reflections of light beams recorded by an image sensor of a camera, which suggest the presence of an individual raindrop in the area of detection.
Figure 4B:
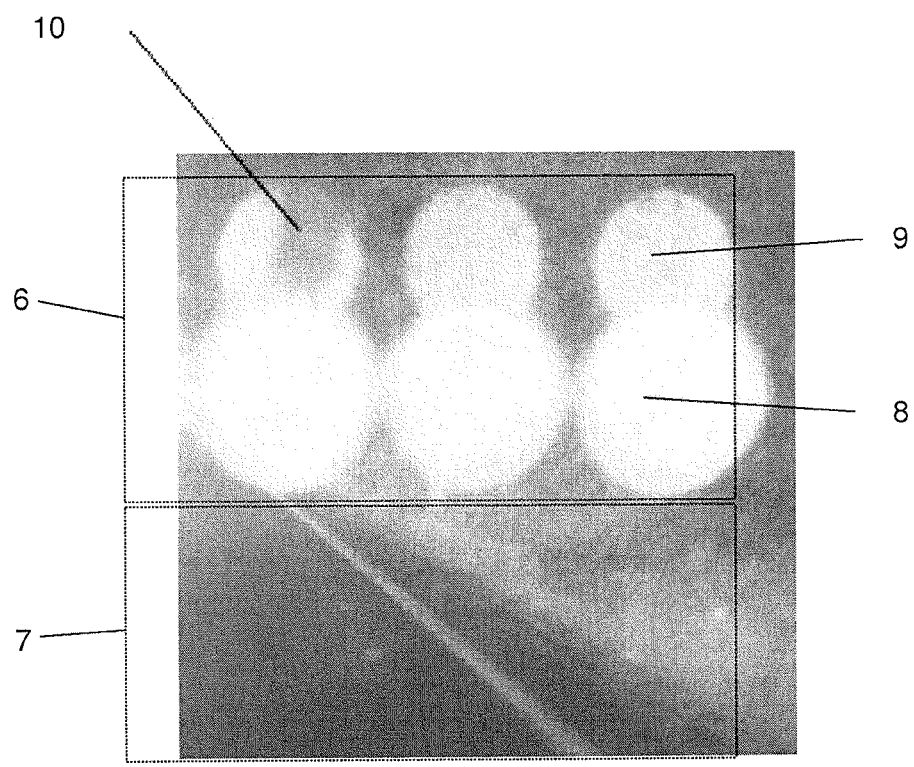

FIGS. 4a and 4b show seven pairs of light reflections (8, 9) in the upper part (6) of the image sensor (5) intended to detect rain, which are e.g. produced by seven LEDs as the light source (3). As the camera (1) is set to infinity focus, these reflections are shown blurred but can be noticed. In particular, the structure of the light reflections can be analyzed. The lower light reflections (8) are produced by beams (r1) which are reflected on the inner side (2.1) of the windscreen (2), the upper light reflections (9) are produced by beams (r2, r2') which are reflected on the outer side of the windscreen.

In order to use the camera image for driver assistance functions at the same time, the pairs of focused light (8, 9) should not interfere with the driver assistance image (7). To this end, an area (6) which is located outside the driver assistance image (7) on the imager (5) is selected for rain detection, based on a suitable arrangement and alignment of the light source (3) and the camera (1) relative to the windowpane (2).

A light reflection (9) from the outer side of the windscreen on which an individual raindrop (4) is located has a dark continuous area or an interruption (10). The intensity of this light reflection (9) is reduced since a large part of the beam (t1) transmitted into the windscreen (2) is coupled out (t2') of the windscreen by the raindrop (4) and is thus not reflected (r2') back to the camera (1). This light reflection (9) therefore contains information as to whether there is rain (4) on the outer side (2.2) of the windowpane (2), and its structure could be used alone as a measuring signal. The analysis may e.g. be done by detecting patterns or by comparing present and stored and/or learned structural characteristics, e.g. dark continuous partial areas or streaks within a light reflection (9). Also, the structures of several of these light reflections (9) may be compared with one another and/or the changes over time of the structure of at least one of these light reflections (9) may be analyzed. Finally, the structure of a reflection from the outer side of the windowpane may be compared with the corresponding reflection from the inner side of the windowpane as a reference structure.

To largely prevent interference caused by the light (3), an infrared-blocking filter may additionally be deposited on a cover glass of the imager (5), up to the upper edge of the driver assistance area (7). Moreover, a band-pass filter for the wavelength of the light (3) may be deposited on the rain sensor detection part (6), as mentioned hereinbefore.

As an alternative, the filters could also be provided directly on the pixels of the image sensor (5). This would have the advantage that a parallax shift caused by the edge of the different filters for the rain sensor area (6) and the driver assistance area (7) on the cover glass would be avoided. It would be advantageous to use a process corresponding to the current application of the pixel colour filters. In this way, the two areas (6, 7) could be separated accurately, to the pixel, thus avoiding additional mechanical tolerance allowances resulting from the production process. At the same time, colour filters (R, G, B) for the rain sensor area (6) would be omitted, thus increasing the sensitivity relating to rain detection.

FIG. 4a is a schematic illustration of the description contained in the above paragraphs. FIG. 4b illustrates this description by means of a real photo (recorded by the image sensor (5) of the camera (1)), which is provided to demonstrate that this embodiment can actually be realized: three blurry light reflections (8 and 9) from the inner side (2.1) and the outer side (2.2) can be seen here, of which the left reflection from the outer side is partially affected by a raindrop.

Figure 5A:
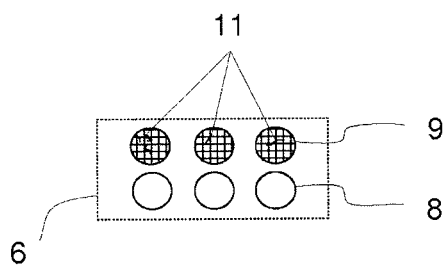
FIGS. 5a and 5b show recorded reflections of light beams which suggest drizzle and/or light rain falling in very fine drops on the windowpane.
Figure 5B:
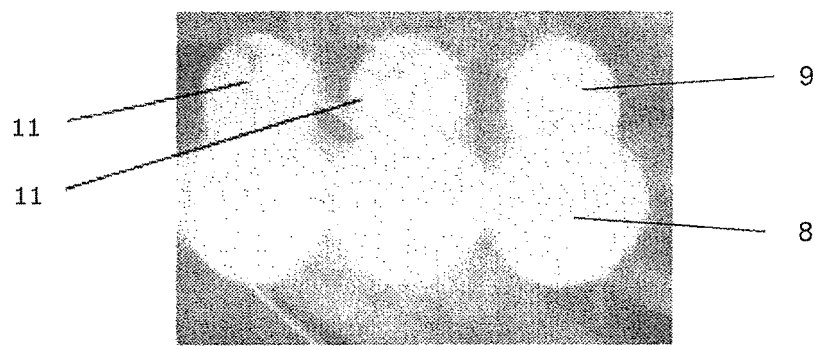

FIGS. 5a and 5b are a principle view of a part of the rain sensor area (6) of the image sensor (5) (cf. FIG. 4) when another type of precipitation (4) is present on the outer side (2.2) of the windscreen (2), namely drizzle or light rain falling in very fine drops. The shown light reflections (9) from the outer side (2.2) of the windowpane (2) contain streaks (11), which are recognized in the analysis of the reflections' structure. If drizzle is present on a larger surface of the outer side (2.2) of the windowpane, there will be streaks on all corresponding light reflections (9).

Again, FIG. 5a is a schematic illustration of the above description, while FIG. 5b illustrates this description by means of a real photo.

Figure 6:
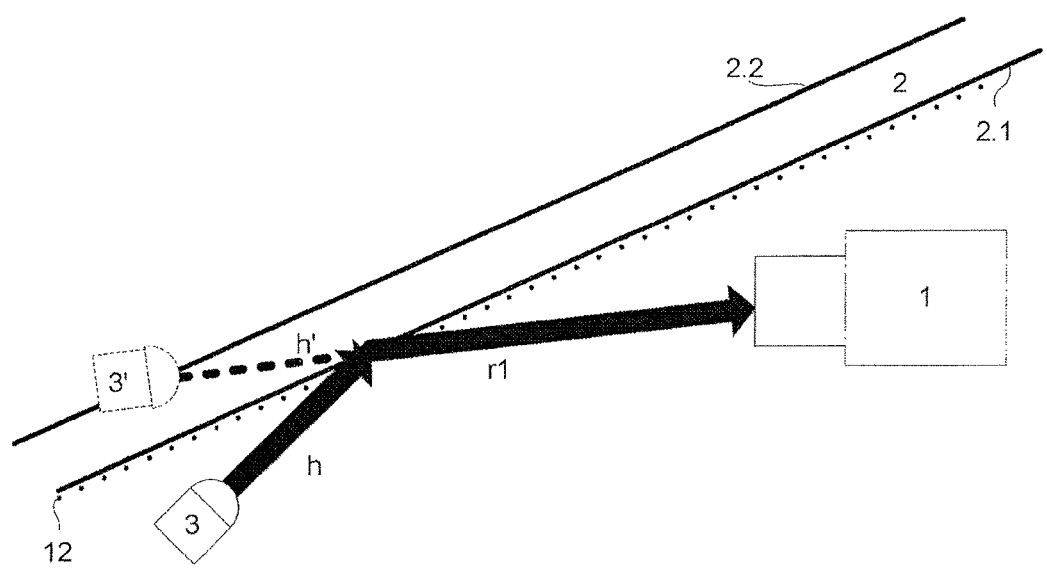
FIG. 6 schematically shows the beam path and a mirror image of the light source in case of condensation and reflection on the inner side of the windowpane.

FIG. 6 schematically shows part of the beam paths (cf. FIGS. 1-3) when there is condensation (12) on the inner side (2.1) of the windowpane (2). In this case, the light reflection (8) appears as a blurry partial beam (r1) which is mirrored on the inner side of the windowpane. The mirror images of the light source (3') and of the light beam (h') are shown schematically by dashed lines.

The condensation on the inner side causes the structure of this light reflection to change, compared to the inner side of a windowpane without condensation. If this structural change of the light reflection (8) from the inner side (2.1) of the windowpane is analyzed, it can be reliably determined whether there is condensation or another circumstance affecting optical characteristics on the inner side of the windowpane. The condensation will, by the way, also affect the light reflection(s) from the outer side of the windowpane.

Figure 7A:
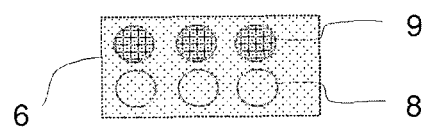
FIGS. 7a and 7b show recorded reflections of light beams which suggest condensation on the inner side of the windowpane.
Figure 7B:
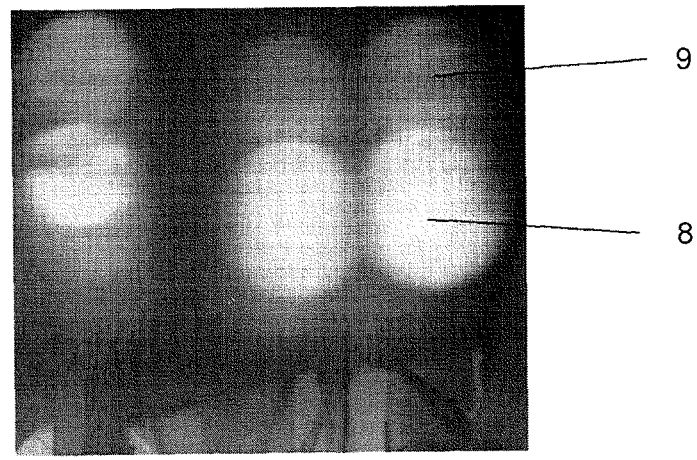

For example, FIGS. 7a and 7b show a part of the rain sensor area (6) of the image sensor (5) (cf. FIG. 5) whose entire surface has a changed image structure, compared to FIGS. 4 and 5, due to condensation (12) on the inner side (2.1) of the windscreen (2). However, it is usually sufficient to analyze the structure of the reflections from the inner side of the windowpane in order to detect condensation or circumstances affecting optical characteristics on the inner side of the windowpane.

Again, FIG. 7a is a schematic illustration of the above description, while FIG. 7b illustrates this description by means of a real photo.

LIST OF REFERENCE SYMBOLS

1 Camera
2 Windowpane
2.1 Inner side of the windowpane
2.2 Outer side of the windowpane
3 Light source
3' Mirror image of the light source
4 Rain, raindrop
5 Image sensor
6 Rain sensor area
7 Driver assistance area
8 Image of the reflection from the inner side of the windowpane
9 Image of the reflection from the outer side of the windowpane
10 Dark partial area
11 Streaks
12 Condensation on the inner side of the windowpane
h Main beam
h' Beam of the mirror image of the light source
r1 Portion of h which is reflected on the inner side of the windowpane
t1 Portion of h which is transmitted on the inner side of the windowpane
r2 Portion of t1 which is reflected on the outer side of the windowpane
t2 Portion of t1 which is transmitted on the outer side of the windowpane
r2' is the same as r2 in case of rain on the outer side of the windowpane
r2' is the same as t2 in case of rain on the outer side of the windowpane

The invention claimed is:

1. A method for detecting rain or precipitation on an outer side of a windowpane, comprising:
arranging a camera behind the windowpane and focusing the camera on a far range in front of the windowpane;
producing, by a light source, for producing at least one light beam (h) which is directed to the windowpane, wherein the light source directs the at least one light beam (h) to the windowpane in such a manner that:
1) at least one beam (r2; r2') is reflected by the outer side of the windowpane and is incident on the camera, and
2) a beam (r1) is reflected by the inner side of the window pane and is incident on the camera, where the beam (r1) is spatially separated from beams (r2; r2');
recording, by the camera an image of the at least one beam (r2; r2') reflected by the outer side of the windowpane and the beam (r1) reflected by the inner side of the windowpane; and
comparing, by an image processing means, the structure of the image of the at least one beam (r2; r2') reflected by the outer side of the windowpane the structure of an image of the at least one beam (r1) reflected by the inner side of the windowpane in order to classify the type of rain or precipitation on the outer side of the windowpane.

2. The method according to claim 1, further comprising:
identifying, by the image processing means, patterns in the structure of the image of the at least one beam (r2; r2') reflected by the outer side of the windowpane.

3. The method according to claim 1, further comprising:
deducing, by the image processing means, the presence of an individual raindrop on the outer side of the windowpane based on a continuous partial area with reduced intensity in the image of the at least one beam (r2; r2') reflected by the outer side of the windowpane.

4. The method according to claim 1, further comprising:
deducing, by the image processing means, the presence of drizzle and/or light rain falling in very fine drops on the outer side of the windowpane based on streaks in the image of the at least one beam (r2; r2') reflected by the outer side of the windowpane.

5. The method according to claim 1, further comprising:
directing, by the light source, the at least one light beam (h) to the windowpane in such a manner that beams (r1; r2 or r2') reflected by an inner side and the outer side of the windowpane are incident on the camera as at least two spatially separated beams (r1; r2 or r2'), and
recording, by the camera, an image of the at least one beam (r2; r2') reflected by the outer side of the windowpane and an image of the beam (r1) reflected by the inner side of the windowpane.

6. The method according to claim 5, further comprising:
detecting, by the image processing means, condensation on the inner side of the windowpane based on tan analysis of the image of the beam (r1) reflected by the inner side of the windowpane.

7. The method according to claim 6, further comprising:
analyzing, by the image processing means, the structure of the image of the beam (r1) reflected by the inner side of the windowpane.

8. The method according to claim 6, further comprising:
analyzing, by the image processing means, the amount of light of the image of the beam (r1) reflected by the inner side of the windowpane.

9. A device for detecting rain or precipitation on a windowpane, comprising:
a camera which is arranged behind the windowpane, which camera is focused on a far range in front of the windowpane;
a light source for producing at least one light beam (h) which is directed to the windowpane, wherein the light source directs the at least one light beam (h) to the windowpane in such a manner that:
1) at least one beam (r2; r2') is reflected by the outer side of the windowpane and is incident on the camera, and
2) a beam (r1) is reflected by the inner side of the windowpane and is incident on the camera, where the beam (r1) is spatially separated from beams (r2; r2');

an image processing means configured to analyze the structure an image of the at least one beam (r2; r2') reflected by the outer side of the windowpane, and compare the structure of the at least one beam (r2; r2') to the structure of an image of the beam (r1) reflected by the inner side of the windowpane in order to classify the type of rain or precipitation on the outer side of the windowpane.

10. The method according to claim 2, further comprising: analyzing, by the image processing means, the structure of the image of the at least one beam (r2; r2') reflected by the outer side of the windowpane by comparing present with stored and/or learned structural characteristics.

11. The method according to claim 7, further comprising: analyzing, by the image processing means, the amount of light of the image of the beam (r1) reflected by the inner side of the windowpane.

12. The method according to claim 1, further comprising: comparing, by the image processing means, present and stored and/or learned structural characteristics of the structure of the image of the at least one beam (r2; r2') reflected by the outer side of the windowpane.

13. The device according to claim 9, wherein the light source directs the at least one light beam (h) to the windowpane in such a manner that the beams (r1; r2 or r2') reflected by an inner side and the outer side of the windowpane are incident on the camera as at least two spatially separated beams (r1; r2 or r2').

* * * * *